(12) United States Patent
Wreschner et al.

(10) Patent No.: US 7,897,351 B2
(45) Date of Patent: Mar. 1, 2011

(54) PEPTIDES AND ANTIBODIES TO MUC 1 PROTEINS

(75) Inventors: Daniel H. Wreschner, Efrat (IL); Nechaama Ina Smorodinsky, Herzelia (IL); Merav Yoeli-Lerner, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 235 days.

(21) Appl. No.: 11/779,012

(22) Filed: Jul. 17, 2007

(65) Prior Publication Data
US 2008/0014210 A1    Jan. 17, 2008

Related U.S. Application Data

(62) Division of application No. 10/473,484, filed as application No. PCT/IL02/00255 on Mar. 26, 2002, now abandoned.

(60) Provisional application No. 60/279,408, filed on Mar. 29, 2001.

(51) Int. Cl.
*G01N 33/53* (2006.01)
*G01N 33/574* (2006.01)
*A61K 39/395* (2006.01)
*A61K 39/00* (2006.01)

(52) U.S. Cl. .................. 435/7.1; 424/130.1; 424/133.1; 424/134.1; 424/138.1; 435/7.2; 435/7.23

(58) Field of Classification Search .................. None
See application file for complete search history.

(56) References Cited

U.S. PATENT DOCUMENTS 5,530,101 A    6/1996    Queen et al.

FOREIGN PATENT DOCUMENTS

| WO | WO 96/03502 | 2/1996 |
| WO | WO 99/40881 | 8/1999 |
| WO | WO 02/22685 | 3/2002 |

OTHER PUBLICATIONS

Rosenblum, Shawver, Marks, Brink, Cheung, and Langton-Webster. Recombinant immunotoxins directed against the c-erb-2/HER2/neu oncogene product: in vitro cytotoxicity, pharmacokinetics, and in vivi efficacy studies in xenograft models. Clinical Cancer Research, 1999. vol. 5, pp. 865-874.*
Hartman et al., *International Journal of Cancer*, 82:256-267 (Jun. 3, 1999).
Zrihan-Licht et al., *European Journal of Biochemistry*, 224 :787-795 (1994).
Price et al., *Tumor Biology*, 19(Suppl. I):1-20 (1998).
Hilkens and Boer, *Tumor Biology*, 19(Suppl. I):67-70 (1998).

* cited by examiner

*Primary Examiner*—Anne M. Gussow
(74) *Attorney, Agent, or Firm*—Browdy and Neimark, PLLC (57) ABSTRACT

The invention relates to methods of inhibiting proliferation or growth of tumor cells and/or inducing cell death in cancer cells. This invention relates to the use of antibodies, hybridomas and pharmaceutical compositions containing same, for inhibiting growth or proliferation and inducing death in epithelial, colon, lung, breast and ovarian tumor cells or other cells which express MUC1 proteins.

12 Claims, 7 Drawing Sheets

BOS 10B3/71(1:4)

Figure 3B

BOS 10D2/36(1:4)

Figure 3C

BOS 7D10/4(1:4)

```
            10         20         30         40         50         60
             |          |          |          |          |          |
        MTPGTQSPFF LLLLLTVLTV VTGSGHASST PGGEKETSAT QRSSVPSSTE KNAVSMTSSV 70         80         90        100        110        120
             |          |          |          |          |          |
        LSSHSPGSGS STTQGQDVTL APATEPASGS AATWGQDVTS VPVTRPALGS TTPPAHDVTS 130        140        150        160        170        180
             |          |          |          |          |          |
        APDNKPAPGS TAPPAHGVTS APDTRPAPGS TAPPAHGVTS APDTRPAPGS TAPPAHGVTS 190        200        210        220        230        240
             |          |          |          |          |          |
        APDTRPAPGS TAPPAHGVTS APDTRPAPGS TAPPAHGVTS APDTRPAPGS TAPPAHGVTS 250        260        270        280        290        300
             |          |          |          |          |          |
        APDTRPAPGS TAPPAHGVTS APDTRPAPGS TAPPAHGVTS APDTRPAPGS TAPPAHGVTS 310        320        330        340        350        360
             |          |          |          |          |          |
        APDTRPAPGS TAPPAHGVTS APDTRPAPGS TAPPAHGVTS APDTRPAPGS TAPPAHGVTS 370        380        390        400        410        420
             |          |          |          |          |          |
        APDTRPAPGS TAPPAHGVTS APDTRPAPGS TAPPAHGVTS APDTRPAPGS TAPPAHGVTS 430        440        450        460        470        480
             |          |          |          |          |          |
        APDTRPAPGS TAPPAHGVTS APDTRPAPGS TAPPAHGVTS APDTRPAPGS TAPPAHGVTS 490        500        510        520        530        540
             |          |          |          |          |          |
        APDTRPAPGS TAPPAHGVTS APDTRPAPGS TAPPAHGVTS APDTRPAPGS TAPPAHGVTS 550        560        570        580        590        600
             |          |          |          |          |          |
        APDTRPAPGS TAPPAHGVTS APDTRPAPGS TAPPAHGVTS APDTRPAPGS TAPPAHGVTS 610        620        630        640        650        660
             |          |          |          |          |          |
        APDTRPAPGS TAPPAHGVTS APDTRPAPGS TAPPAHGVTS APDTRPAPGS TAPPAHGVTS 670        680        690        700        710        720
             |          |          |          |          |          |
        APDTRPAPGS TAPPAHGVTS APDTRPAPGS TAPPAHGVTS APDTRPAPGS TAPPAHGVTS 730        740        750        760        770        780
             |          |          |          |          |          |
        APDTRPAPGS TAPPAHGVTS APDTRPAPGS TAPPAHGVTS APDTRPAPGS TAPPAHGVTS 790        800        810        820        830        840
             |          |          |          |          |          |
```

FIG 5. CONT.

```
           APDTRPAPGS TAPPAHGVTS APDTRPAPGS TAPPAHGVTS APDTRPAPGS TAPPAHGVTS 850        860        870        880        890        900
                   |          |          |          |          |          |
           APDTRPAPGS TAPPAHGVTS APDTRPAPGS TAPPAHGVTS APDTRPAPGS TAPPAHGVTS 910        920        930        940        950        960
                   |          |          |          |          |          |
           APDTRPAPGS TAPPAHGVTS APDTRPAPGS TAPPAHGVTS APDNRPALGS TAPPVHNVTS 970        980        990       1000       1010       1020
                   |          |          |          |          |          |
           ASGSASGSAS TLVHNGTSAR ATTTPASKST PFSIPSHHSD TPTTLASHST KTDASSTHHS 1030       1040       1050       1060       1070       1080
                   |          |          |          |          |          |
           SVPPLTSSNH STSPQLSTGV SFFFLSFHIS NLQFNSSLED PSTDYYQELQ RDISEMFLQI 1090       1100       1110       1120       1130       1140
                   |          |          |          |          |          |
           YKQGGFLGLS NIKFRPGSVV VQLTLAFREG TINVHDVETQ FNQYKTEAAS RYNLTISDVS 1150       1160       1170       1180       1190       1200
                   |          |          |          |          |          |
           VSDVPFPFSA QSGAGVPGWG IALLVLVCVL VALAIVYLIA LAVCQCRRKN YGQLDIFPAR 1210       1220       1230       1240       1250       1255
                   |          |          |          |          |          |
           DTYHPMSEYP TYHTHGRYVP PSSTDRSPYE KVSAGNGGSS LSYTNPAVAA ASANL
```

Figure 6

SVV VQLTLAFREG TINVHDVETQ FNQYKTEAAS RYNLTISDVS
VSDVPFPFSA QSGAGV

PEPTIDES AND ANTIBODIES TO MUC 1 PROTEINS

FIELD OF THE INVENTION

The invention relates to methods of inhibiting proliferation or growth of tumor cells and/or inducing cell death in cancer cells. This invention relates to the use of antibodies, hybridomas and pharmaceutical compositions containing same, for inhibiting growth or proliferation and inducing death in epithelial, colon, lung, breast and ovarian tumor cells or other cells which express MUC1 proteins.

BACKGROUND OF THE INVENTION

Tumor markers are molecules that are associated with the transformation of a normal cell into a malignant cell. Tumor markers are either altered proteins which are different from the proteins expressed in normal cells or over-expression of proteins that are not expressed, or slightly expressed in normal cells.

Mucins are high molecular weight glycoproteins, which are produced by normal epithelial cells. MUC1 is one of the four mucins known to date that are transmembrane molecules and while its function in adult life maybe lubrication, in fetal life development it is thought to play an important role in forming the lumen of the duct by keeping apart cells located opposite one another. The MUC1 gene was also shown to be expressed in hemopoietic tissues. It was found that MUC1 (also called H23-Ag, episialin, PEM—Polymorphic Epithelial Mucin, MCA—Mammary Carcinoma Antigen and EMA Epithelial Membrane Antigen) expression is elevated (10-50 fold) in breast cancer cells in comparison to normal resting mammary secretory epithelial cells. Moreover, immunohistochemical analyses using the H23 mAb (which recognizes MUC1), revealed that MUC1 is expressed in 91% of the breast cancer tissues and 100% of breast cancer metastases, whereas the non-malignant tissues were negative for the H23 mAb staining (1). Elevated levels of the MUC1 protein in serum and body fluids were reported in 7%, 17%, 64% and 67% of breast cancer patients presenting with stages I to IV, respectively. In addition, elevated levels of circulating MUC1 may be associated with a poor prognosis.

It was shown that MUC1 is over expressed in epithelial cancers other than breast cancer. MUC1 was shown to be over expressed in epithelial ovarian cancer cells as well as in all types of lung cancer cells and other cancers (2).

In malignancy, the MUC1 oligosacharide chains are shorter and less dense comparing to MUC1 in normal cells. This results in the exposure of new epitopes of the core protein in the cancer-associated mucin.

Isolation of MUC1 cDNAs revealed several protein isoforms: the MUC1/REP, MUC1/SEC MUC1/Y and MUC1/X proteins. A short description of four of the above-mentioned isoforms that are connected with the present invention is given below:

The MUC1/REP isoform is a transmembrane protein that contains: a large extracellular domain consisting of a heavily glycosylated 20 amino acid repeat motif. The number of these repeats varies from 20 to 100 and thus is named a VNTR (Variable Number of Tandem Repeats); a transmembrane domain, which consists of a 28 amino acid hydrophobic sequence, and a 72 amino acid cytoplasmic domain. During the biosynthesis of the MUC1/REP protein it undergoes a proteolytic cleavage event. The cleavage takes place within the conserved sequence IKFRPGSWV (SEQ ID NO:3) that is contained within the extracellular domain. Intriguingly, this cleavage site resides within a previously identified module, designated the "SEA" module (3), found in a number of highly 0-linked glycosylated proteins that are invariably linked in one way or another to the cell membrane. The SEA module functions not only as a site for proteolytic cleavage, but also for subsequent re-association of the subunits. Consequently, the MUC1/REP protein is presented on the cell surface as a heterodimer which is composed of a large extracellular subunit (containing the repeat array) linked by non-covalent, SDS sensitive bonds to a smaller cell-anchored subunit which consists of a small extracellular fragment followed by the transmembrane and cytoplasmic domains. The large extracellular subunit can disconnect and reconnect with the small extracellular fragment of the cell-anchored subunit.

The MUC1/Y isoform is a transmembrane protein that contains transmembrane and cytoplasmic domains identical to those of MUC1/REP protein. Unlike MUC1/REP, due to a differential splicing event that utilizes splicing sites located upstream and downstream to the repeat array, MUC1/Y protein is devoid of both the tandem repeat array and its flanking regions. Expression of MUC1/Y was demonstrated in various human secretory epithelial tumors. MUC1/Y was found to be expressed on the cell surface of various human epithelial tumor cells but is not detectable in the adjacent normal tissue.

The MUC1/X isoform (4) is a transmembrane protein that contains transmembrane and cytoplasmic domains identical to those of MUC1/REP protein. Unlike MUC1/REP, due to a differential splicing event that utilizes splicing sites located upstream and downstream to the repeat array, MUC1/X protein is devoid of both the tandem repeat array and its flanking regions.

The MUC1/SEC isoform: This isoform is generated by an alternative splicing mechanism. It is a secreted protein since it lacks the hydrophobic region that can attach the protein to the cell membrane. Its N-terminal sequences are identical to those of the MUC1/REP extracellular domain. Furthermore it has been shown that the soluble secreted MUC1/SEC protein may bind specifically to the extracellular domain of the MUC1/Y protein (5).

Thus, it will be highly advantageous to develop a ligand which binds to a specific epitope in the MUC1 proteins and, more particularly, to a specific extracellular epitope in the MUC1/REP or MUC/Y proteins that will dramatically inhibit the proliferation or growth of cells, and will induce death in cells, such as, cancer cells and in particular cells which over express MUC1 proteins.

SUMMARY OF THE INVENTION

In one embodiment, this invention provides methods for inhibiting cell proliferation or growth and/or inducing cell death in cancer cells and in particular in epithelial, breast, colon, lung and ovarian tumor cells which express MUC1 proteins.

In one embodiment, the invention provides a method of selectively inhibiting the proliferation or cell growth of cells, comprising the step of administering to a subject, an effective amount of a ligand which specifically binds to an epitope in the extracellular region of a transmembrane isoform of MUC1 protein, thereby selectively inhibiting proliferation or growth of such cells.

In one embodiment, the invention further provides a method of inducing cell death comprising the step of administering to a subject, an effective amount of a ligand which specifically binds to an epitope in the extracellular region of a transmembrane isoform of MUC1 protein, thereby selectively inducing cell death.

In one embodiment, the invention provides a method of selectively inhibiting cell proliferation or cell growth comprising the step of contacting a cell which expresses MUC1 protein isoform with an effective amount of a ligand which specifically binds to an epitope in the extracellular region of the transmembrane isoform of MUC1 protein, thereby selectively inhibiting the cell proliferation or cell growth.

The invention provides a method of inducing cell death comprising the step of contacting a cell which expresses MUC1 protein isoform with an effective amount of a ligand which specifically binds to an epitope in the extracellular region of the transmembrane isoform of MUC1 protein, thereby selectively inducing cell death.

In one embodiment, the invention further provides a method of treating a subject with a disease involving pathological proliferation of cells comprising the step of administering to a subject, an effective amount of a ligand which specifically binds to an epitope in the extracellular region of a transmembrane isoform of MUC1 protein, thereby treating the disease.

In one embodiment, the invention further provides a method of treating a subject with a disease involving pathological proliferation of cells comprising the step of administering to a subject, an effective amount of a peptide which comprises an amino acid sequence corresponding to the extracellular region of a transmembrane isoform of MUC1 protein, so as to induce an increase in the level of antibodies specific for said peptide in the subject, thereby treating the disease.

In one embodiment, the invention further provides an isolated antibody which specifically binds to an epitope in the extracellular region of an isoform of MUC1 protein wherein said epitope is located within a 59 amino acid sequence according to the amino acid sequence of SEQ ID No. 1.

In one embodiment, the invention further provides a pharmaceutical composition comprising an effective amount of a ligand, which specifically binds to a MUC1 protein isoform, and a pharmaceutically acceptable carrier.

In one embodiment, the invention further provides a hybridoma cell producing monoclonal antibody that binds to an epitope in the extracellular region of an isoform of MUC1 protein. In one embodiment the epitope is located within a 59 amino acid sequence according to the amino acid sequence of SEQ ID No. 1 and is located directly N'-terminal to the transmembrane domain of the protein.

BRIEF DESCRIPTION OF THE DRAWINGS

The present invention will be understood and appreciated more fully from the following detailed description taken in conjunction with the appended drawings in which:

FIG. 3 A-D show the effect of anti-MUC1 monoclonal antibodies on the growth of H/Y2 cells (A) using MTT assay and (B-D) by assessing the cell morphology by microscope.

DETAILED DESCRIPTION OF THE INVENTION

MUC1 is one of the four mucins which are transmembrane glycoproteins produced by normal epithelial cells. As was described before, its expression is markedly increased in all human breast cancer and other epithelial cancer cells. The sequence of MUC1 is demonstrated on FIG. 5.

The terms "specific binding" or "specifically bind" hereinabove in the specifications and in the claims section refer to the interaction between a protein, a peptide, an agonist, an antibody, or an antagonist. The interaction is dependent upon the presence of a particular structure of the protein, e.g., the antigenic determinant or epitope, recognized by the binding molecule.

In another embodiment the ligand can be an antibody, antibody fragments, an antagonist, an agonist or a peptide.

The term "contacting the cell" refers herein above in the specification and in the claims refers to administering the cell, or exposing the cell to the ligand, which binds to a specific epitope on MUC1/Y or MUC1/X or MUC1/REP by methods of direct application, which are known in the art. The ligand can be applied before or after the seeding of the cells.

The term "antagonist" refers to a molecule which, when bound to the epitope, decreases the amount or the duration of the effect of the biological or immunological activity of epitope. Antagonists may include proteins, nucleic acids, carbohydrates, antibodies, antisense or any other molecules which decrease the effect of MUC1 epitope on cell growth or cell viability.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; single-chain antibody molecules; and multispecific antibodies formed from antibody fragments.

The term "agonist" refers hereinabove in the specifications and in the claims to any molecule which, when bound or activate the epitope, increases the amount or the duration of the effect of the biological or immunological activity of epitope. The molecule can be a peptide or a nucleic acid construct.

As demonstrated herein, Applicants unexpectedly discovered the effect of the antibody BOS7D10 on cell growth and/or proliferation which is clearly exemplified in Example 2 and in FIG. 3. The effect of this antibody and other antibodies to MUC1/Y and MUC1/SEC on cell viability was assessed by MTT assay and by using a microscope, which are well known methods in the art. The effect of BOS7D10 which is directed to an epitope which is included in the 59 amino acid sequence as set forth on SEQ ID No. 1, wherein the 59 amino acids sequence is located directly N-terminal to the transmembrane domain of the MUC1/Y protein isoform and MUC1/X protein isoform and MUC1/REP protein isoform, was dramatic in comparison to other antibodies which bind to different epitopes on the same protein.

Figure 3A:
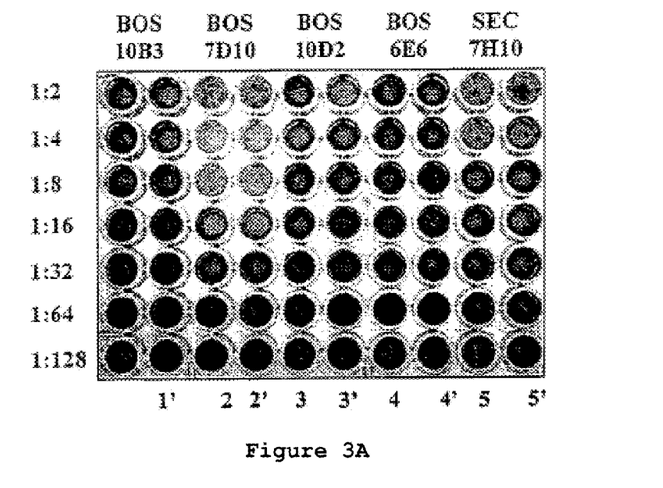

The term "selectively inhibiting cell proliferation or cell growth" as used hereinabove in the specifications and in the claims, means killing or reducing growth i.e. differentiation, or proliferation i.e. propagation of pathologically proliferating cells without causing unacceptable killing or reduction of growth or proliferation of normal cells. In one embodiment, the killing or reducing growth i.e. differentiation, or proliferation i.e. propagation of pathologically proliferating cells is by at least 20%. The antibody described in the invention was shown as a potent agent for inhibiting the proliferation (FIG. 3A).

"Selectively inducing cell death" refers hereinabove in the specifications and in the claims, to cause a reduction in the viability of the pathological cells by at least 20%. The cell death can be demonstrated by methods of assessing cell viability such as morphology or use of different dyes such as MTT assay or Propidium Iodide (PI) staining, trypan blue assay, pre-cytolytic DNA fragmentation, alterations in membrane asymmetry, activation of apoptotic caspases and release of cytochrome C into the cytoplasm by mitochondria, degradation of actin filaments which are well known to someone who is skilled in the art.

There can be many processes by which cell death is achieved and some of these can lead to apoptosis. There is speculation that there are other cell death mechanisms other than apoptosis but regardless of how the cell arrives at death there are some characteristics of cell death. One of these is the absence of metabolism and another is the denaturation of enzymes. In either case vital stains will fail to stain these cells. These endpoints of cell death have been long understood and predate the current understanding of the mechanisms of cell death. Furthermore, there is the distinction between cytotoxic effects where cells are killed and cytostatic effects where the proliferation of cells are inhibited. According to the data shown in the Examples section, the antibody of the invention is efficient as a cytotoxic agent as well as a cytostatic agent and is considered as an apoptotic antibody.

The "cell" of the present invention refers in the specification and in the claims section to a pathologically proliferating cell such as cancer cells which according to another embodiment of the invention express MUC/1 proteins. In another embodiment the MUC1 proteins are over expressed.

The cancer cell may be, without being limited, an epithelial cell, a breast cancer cell, a colon cancer cell, a lung cancer cell or any cell, which expresses MUC1 protein isoforms. MUC1 protein isoforms comprises, without being limited, protein isoforms such as MUC1/Y, MUC1/X, MUC1/REP and MUC1/SEC proteins. "Isoforms" are proteins that are translated from the same gene but due to post translational or post transcriptional modifications, may contain different number of amino acids and/or different additional groups and/or have a different molecular structure.

MUC1/Y, MUC1/X and MUC1/REP have identical transmembrane and cytoplasmic domains. More important, the domain located N'-terminal to the transmembrane domain is identical in these two isoforms (red box in FIG. 2) Thus, the antibodies of the invention can bind to an epitope, which exist on both protein isoforms.

The term "epitope" refers to the particular part of the antigen makes contact with a particular antibody. According to an embodiment of the invention, the epitope length is 4-12 amino acids. In another embodiment the epitope length is 5-10 amino acids, in yet another embodiment the epitope length is 6-8 amino acids. The epitope sequence is included within the 59 amino acid sequence as set forth in SEQ ID No. 1 and below:

(N-terminus) SVV VQLTLAFREG TINVHDVETQ FNQYKTEAAS
RYNLTISDVS VSDVPFPFSA QSGAGV (C-terminus)

In another embodiment the epitope is located in the 15 amino acid sequence that resides at the N-terminal portion of the 59 amino acid segment which is located directly N-terminal to the transmembrane domain of the MUC1/Y, MUC1/X and MUC1/REP proteins. The epitope is located in the extracellular region of the transmembrane isoform of the MUC1/Y, MUC1/X and MUC1/REP proteins.

The term "extracellular region" refers hereinabove in the specification and in the claims to a strech of a variable number of amino acids located directly N-terminal to the transmembrane domain and appears in the extracellular environment.

The term "transmembrane" refers hereinabove in the specification and in the claims to a strech of amino acids, mostly hydrophobic, located within the membrane, N-terminal to the cytoplasmic domain and C-terminal to the extracellular domain of the protein. This domain enables the anchor of the protein to the membrane.

The term "antibody" refers hereinabove in the specification and in the claims to an immunoglobulin whether natural or partly or wholly synthetically produced. The antibodies can be human or animalic antibodies. The term also covers any polypeptide or protein having a binding domain which is, or is homologous to, an antibody binding domain. These can be derived from natural sources, or they may be partly or wholly synthetically produced. Examples of antibodies are the immunoglobuiin isotypes and their isotypic subclasses; fragments which comprise an antigen binding domain such as Fab, scFv, Fv, dAb, Fd; and diabodies. As is examplified on Example 2, the antibody BOS7D10 showed a potent inhibitory effect on cell growth as well as a potent cell death activity on MCF7.

It is possible to take monoclonal and other polyclonal antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GE 2188638A or EP-A-239400. As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

It has been shown that fragments of a whole antibody can perform the function of binding antigens. Examples of binding fragments are (i) the Fab fragment consisting of VL, VH, CL and CHI domains; (ii) the Fd fragment consisting of the VH and CHI domains; (iii) the Fv fragment consisting of the VL and VH domains of a single antibody; (iv) the dAb fragment (8) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (9-10). (viii) bispecific single chain Fv dimers (PCT/US92/09965) and (ix) "diabodies", multivalent or multispecific fragments constructed by gene fusion (WO94/13804; (11). Diabodies are multimers of polypeptides, each polypeptide comprising a first domain comprising a binding region of an immunoglobulin light chain and a second domain comprising a binding region of an immunoglobulin heavy chain, the two domains being linked (e.g. by a peptide linker) but unable to associate with each other to form an antigen binding site: antigen binding sites are formed by the association of the first domain of one polypeptide within the multimer with the second domain of another polypeptide within the multimer (WO94/13804).

One of the potential benefits of monoclonal antibodies with respect to the treatment of cancer is their ability to specifically recognize single antigens. It was thought that in some instances cancer cells possess antigens that were specific to that kind of transformed cell. It is now more frequently believed that cancer cells have few unique antigens, rather, they tend to over-express a normal antigen such as MUC1 proteins or express fetal antigens. Nevertheless, the use of monoclonal antibodies provided a method of delivering reproducible doses of antibodies to the patient with the expectation of better response rates than with polyclonal antibodies.

As exemplified in Example 3, a surprising, unexpected correlation has been found between the effect of the antibodies on the interaction of MUC1/SEC and MUC1/Y and their effect on cell death. An antibody that was potent in inducing cell death was also potent in inducing interaction between the isoforms and vice versa (see table 1). This surprising correlation may be related to the mechanism of action of the antibody in inducing cell death.

The invention further provides an isolated antibody, which binds to the described epitope. The antibody can be a monoclonal antibody, a synthetic antibody, a polyclonal antibody or a chimera e.g., mouse variable regions joined to human constant regions.

In another embodiment this invention provides a method of treating a subject with a disease involving pathological proliferation of cells comprising the step of administering to a subject in need an effective amount of a peptide comprising an amino acid sequence corresponding to the extracellular region of a transmembrane isoform of MUC1 protein, said peptide is for example a 59 amino acid sequence of SEQ ID No. 1 which is located directly N'-terminal to the transmembrane domain of the MUC1 protein. According to the invention, said peptide induces an increase in the level of antibodies specific for said peptide in the subject. The term "induces an increase in the level of antibodies specific for said peptide" refers to an increase in the level of specific antibodies directed against said peptide above the basal level of said antibodies in non-treated subject.

Figure 6:
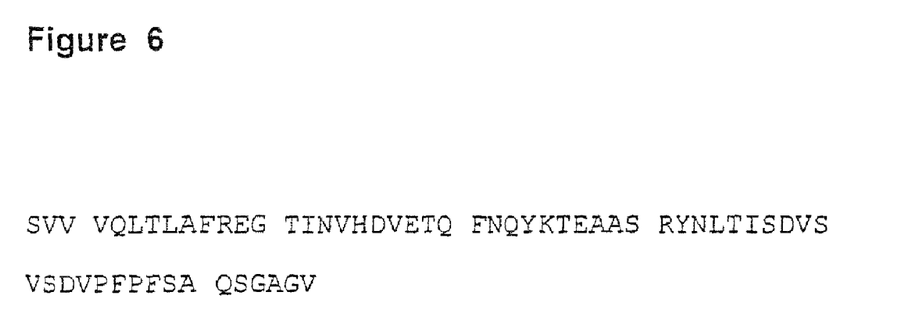
FIG. 6 demonstrates the 59 amino acid sequence (SEQ ID NO:1) that includes the epitope recognized by the BOS7D10 monoclonal antibodies.

The amino acid sequence of the region that includes the epitope of the antibody is shown in FIG. 6. BOS7D10 has been deposited at the European Collection of Cell Cultures, Porton Down, Salisbury SP4 OJG, UK under Accession number 03102901.

The terms "amino acid" or "amino acid sequence" refer to an oligopeptide, peptide, polypeptide, or protein sequence, or a fragment of any of these, and to naturally occurring or synthetic molecules.

The invention further provides a pharmaceutical composition comprising an amount of a ligand (such as an antibody, a peptide or an antagonist), which specifically binds to MUC1 protein isoforms and a pharmaceutically acceptable carrier.

The term "pharmaceutically acceptable carrier" refers to a carrier or a diluent that does not cause significant irritation to an organism and does not abrogate the biological activity and properties of the administered compound.

The invention methods and ligands can be further extended to treat mammals and especially humans with diseases involving pathological proliferation of mammalian cells such as cancer. To "treat" refers to: (i) preventing a disease, occurring in an animal that may be predisposed to the disease, disorder and/or condition, but has not yet been diagnosed as having it; (ii) inhibiting the disease i.e., arresting its development; and (iii) relieving the disease i.e., causing regression of the disease.

Thus, the invention further provides a method of inhibiting pathological proliferation of mammalian cells or cell growth comprising the step of administering to a subject in need, an effective amount of a ligand which specifically binds to an epitope in the extracellular region of a transmembrane isoform of MUC1 protein thereby selectively inhibiting pathological proliferation or growth of mammalian cells.

In another embodiment the invention provides a method of inducing cell death comprising the step of administering to a subject in need, an effective amount of a ligand, which specifically binds to an epitope in the extracellular region of a transmembrane isoform of MUC1 protein thereby inducing cell death.

The step of administering may involve either direct injection of the ligand with a pharmaceutically acceptable carrier that will be targeted to the target cells. Alternatively, a prodrug may be used that will be activated only in the required target cells either by different enzymes or by different chemical-physical conditions.

Liposomes have been used successfully to administer medications to cancer patients, and have been shown to be useful clinically in the delivery of anticancer drugs such as doxorubicin, daunorubicin, and cisplatinum complexes (12-14).

Similarly, micelles have also been used to deliver medications to patients, (15) and micelles have been used as drug carriers and for targeted drug delivery, (16-17) including cancer medications, (18-19).

If the antibody or composition is suitable for oral administration the formulation may contain, in addition to the active ingredient, additives such as: starch e.g. potato, maize or wheat starch or cellulose or starch derivatives such as microcrystalline cellulose; silica; various sugars such as lactose; magnesium carbonate and/or calcium phosphate. It is desirable that, if the oral formulation is for administration it will be well tolerated by the patient's digestive system. To this end, it may be desirable to include in the formulation mucus formers and resins. It may also be desirable to improve tolerance by formulating the antibody or compositions in a capsule which is insoluble in the gastric juices. It may also be preferable to include the antibody or composition in a controlled release formulation.

If the antibody or composition is suitable for rectal administration the formulation may contain a binding and/or lubricating agent; for example polymeric glycols, gelatins, cocoa-butter or other vegetable waxes or fats.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means. Alternatively, the antibody or composition may be in dry form, for reconstitution before use with an appropriate sterile liquid.

In addition to the active ingredients, these pharmaceutical compositions may contain suitable pharmaceutically acceptable carriers comprising excipients and auxiliaries, which facilitate processing of the active compounds into preparations, which can be used pharmaceutically. Further details on techniques for formulation and administration may be found in the latest edition of Remington's Pharmaceutical Sciences (Maack Publishing, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i e., dosage.

Pharmaceutical preparations, which can be used orally, include push-fit capsules made of gelatin, as well as soft sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances, which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

After pharmaceutical compositions have been prepared, they can be placed in an appropriate container and labeled for treatment of an indicated condition.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans. Effective dose is determined also in clinical trials in humans.

The ligand of the invention is capable of promoting the interaction of MUC1/Y with MUC1/SEC. The change in morphology was observed in FIG. 3B-D and might be related to the interaction of these two isoforms, wherein MUC1/SEC serves as a ligand to MUC1/Y which behaves as the receptor.

The term "cancer" is interpreted broadly. The ligand, such as antibody or antagonist, of the invention can be "anti-cancer agent", which term also encompasses "anti-tumor cell growth agent" and "anti-neoplastic agent". For example, the methods of the invention are useful for treating cancers by inducing cell death or by inhibiting the pathological cell proliferation/ or growth.

The invention further provides a hybridoma cell producing monoclonal antibody that binds to an epitope in the extracellular region of an isoform of MUC1 protein.

The hybridomas producing the monoclonal antibodies of the present invention are produced following the general procedures described by Kohler and Milstein, Nature, 256, p. 495 (1975). In that procedure, hybridomas are prepared by fusing antibody producing cells (typically spleen cells of mice previously immunized with a mucin antigen source) to cells from an immortal tumor cell line using somatic cell hybridization procedures. The agents used for immunization of animals ("immunogens") to induce production of antibodies to mucin antigens.

For the production of antibodies, various hosts including goats, rabbits, rats, mice, humans, and others may be immunized by injection with the relevant epitope or with any fragment or oligopeptide thereof, which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable Freund's adjuvant.

The hybridomas resulting from the fusion process are allowed to grow. Thereafter, the resulting supernatants are screened using immunoassay procedures to detect antibodies present in the supernatants capable of binding to the specific antigens. In other cases, supernatants were screened for their ability to bind cultured cancer cells.

The antibodies are designed for therapeutic treatment of cancer in patients. Thus, the antibodies can be naked antibodies. In another embodiment, the antibodies can be conjugated to a cytotoxic drug. The term cytotoxic drug refers to any agent which kills cells for example, without being limited, a radioactive isotope. The antibodies can be used to target other molecules to the cancer cells. Examples for cytotoxic drugs are without being limited bromodeoxyuridine (BUdR), 5-iododeoxyuridine (IUdR), bromodeoxycytidine, fluorodeoxyuridine (FudR), hydroxyurea, cisplatin.

It will be appreciated that the present invention is not limited by what has been described and that numerous modifications, all of which fall within the scope of the present invention, exist. For example, while the present invention has been described with respect to the tested antibody, it could be that other antibodies which overlap part of the epitope described will demonstrate similar effect.

It will be appreciated by persons skilled in the art that the present invention is not limited by what has been particularly shown and described herein above.

EXAMPLES

Materials and Methods

Cell Lines

HBL-100—An epithelial cell line was obtained from primary cultures of cells derived from an early lactation sample of human milk (20). The cells contain a tandemly integrated SV40 genome.

HBL/neo (H/N)—Stable transfectants generated by transfecting the cloning vector pSV2neo to the HBL-100 cells.

HBL/Y2 (H/Y2)—Stable transfectant generated by co-transfecting the expression plasmid harboring the MUC1/Y cDNA and the cloning vector pSV2neo.

Media for Cell Culture Growth

The DMEM growth medium (Dulbecco's modified Eagle's medium) was purchased from Biological Industries, Kibbutz Beit Haemek, Israel.

Media Supplements:

Antibiotics: 10 µg/ml Nystatin, 100 µg/ml Streptomycin, 100 µg/ml Ampicillin. (Biological industries, Kibbutz Beit Haemek, Israel).

4 mM L-Glutamine (Biological industries, Kibbutz Beit Haemek, Israel).

Heat inactivated (56° C. for 30 min.) 10% fetal calf serum (FCS) (Biological industries, Kibbutz Beit Haemek, Israel).

The mixture Oxaloacetate (Sigma), Pyruvate (Sigma), Insulin (Sigma) (OPI) was added to the growth medium of the hybridoma cells.

Hybridoma S.M (serum free) medium—DMEM growth medium (Dulbecco's modified Eagle's medium) was diluted 1:1 with the F12 medium (Biological industries, Kibbutz Beit Haemek, Israel) and supplemented with the antibiotics (10? g/ml Nystatin, 100 µg/ml Streptomycin, 100 µg/ml Ampicillin), 4 mM L-Glutamine and "BIOGRO-2", synthetic serum free medium supplement. All the above materials were purchased from Biological Industries, Kibbutz Beit Haemek, Israel.

Flow cytometry medium—DMEM supplemented with the antibiotics described above, 5% FCS and 0.01% Na-Azide.

Antibodies

H23—Monoclonal antibody that recognizes an epitope within the MUC1 tandem repeat array thus, it can detect MUC1/REP and MUC1/SEC.

BOS6E6—Anti-MUC1/Y specific monoclonal antibody, that recognizes the MUC1/Y unique epitope.

BOS7D10, BOS10D2, BOS10B3—Monoclonal antibodies that recognize epitopes within the MUC1/Y extracellular domain.

SEC7H10—Anti MUC1/SEC specific mAb, that recognizes the MUC1/SEC C-terminal eleven amino acids.

Cell Culture

Growing Cells in Culture:

Cell were cultured in 25 $cm^2$ or 75 $cm^2$ tissue culture flasks (Falcon Costar) with 5 ml or 10 ml culture medium respectively and kept in an incubator, at 37° C., 95% air and 5% $CO_2$.

Harvesting and Seeding of Cells:

Harvesting of cells growing in monolayer was performed by addition of 0.5-1 ml of Trypsin-EDTA solution to the flask for 1-5 minutes (cell type preference). Subsequently, an equal amount of 10% FCS rich growth medium was added to neutralize enzyme activity. Cells were seeded in tissue culture flask containing growth medium.

Cell Counting:

Cells were counted using a hemocytometer. Cells were re-suspended in a medium containing 0.08% Trypan blue in order to detect dead cells.

Cell Transfections.

Cell transfection was performed using the following commercial transfection kit: DOTAP Transfection reagent kit (Roche diagnostics), Effectene Transfection Reagent (Qiagen) and LipofectAMINE Transfection reagent (Gibco-BRL). The transfection protocols were performed according to the manufacturer manual.

Flow-Cytometry Analysis (FACS Analysis).

Cell samples ($10^6$ cells/sample), were washed with flow cytometry medium and incubated for 2 hours at 4° C., with primary antibody diluted in flow cytometry medium. Cells were washed with flow cytometry medium and incubated for 45 min at 4° C. with the secondary anti mouse-FITC conjugate antibody, (diluted 1:50 in Flow cytometry medium) followed by extensive washing and cells resuspended in PBS containing 0.01% Na-Azide. The samples were analyzed by FACS Analyser (Beckton Dickenson). The flow cytometry results were analyzed using the "Cell Quest" software.

MTT Proliferation Assay.

20 µl of 0.5% MTT (Sigma) solution (in phosphate saline buffer), were added to HBL-Y cells growing in 200 µl medium in 96 wells plate. Cells were incubated with the MTT reagent for 2 h at 37° C., medium was removed from the cells, and the MTT crystals were dissolved for 15 minutes in 95% ethanol and plates were read by the ELISA reader at 592 nm.

MUC1/SEC-MUC1/Y Interaction Elisa Assays 96 Micro-Titer.

"Maxi Sorp" plates (NUNC) were coated over night at room temperature with 100 µl conditioned medium containing MUC1/SEC. Following coating plates were washed twice with phosphate saline washing buffer containing 0.05% Tween 20 (0.05%) pH 7.0 (neutralized with 1M HCl) and blocked for 2 h at 35° C. with phosphate saline washing buffer supplemented with 10% FCS. Recombinant MUC1/Y diluted in phosphate saline washing buffer supplemented with 10% FCS was incubated in plates for 2hr at 35° C. Following incubation the plate was extensively washed with phosphate saline washing buffer, and incubated for additional 2 hr at 35° C. with biotinylated 6E6/2 mAb diluted 1:300 in phosphate saline washing buffer followed by extensive wash with phosphate saline washing buffer, and incubation with Streptavidin-HRP (diluted 1:1000). The reaction was developed with the OPD substrate (Sigma). The reaction was stopped by addition of 30 µl of 2M Sulfuric acid and read at 490 nm.

Vectors

SV2neo—Vector encoding the neomycin resistance gene allowing stably transfected eukaryotic cells to be selected using G418 (21)

pCL642-MUC1/Y—pCL642 coding for the MUC1/Y isoform (6).

DNA Ligation.

Reaction was performed by incubating the following mixture, at a gradually decreasing temperature from 25° C. to 4° C. for over-night.

| | |
|---|---|
| DDW | As required |
| 10 × T4 reaction buffer (NEB) | X1 |
| Plasmid DNA | ~100 ng |
| DNA Insert | 3 × molar access of plasmid |
| T4 DNA ligase (NEB) | 1 unit |
| Total volume | 20 µl |

Plasmid Preparation

Both small and large-scale plasmid preparation (Mini and Maxi preps. respectively) were performed according to Maniatis handbook (Smbrook et al., 1990).

DNA concentration was determined by translating optical density (OD) units at 260 nm according to the following formula: $1O.D_{260\ nm}=40\ \mu g$ Example 1

Establishment of MUC1/Y Expressing Cells

Figure 1:
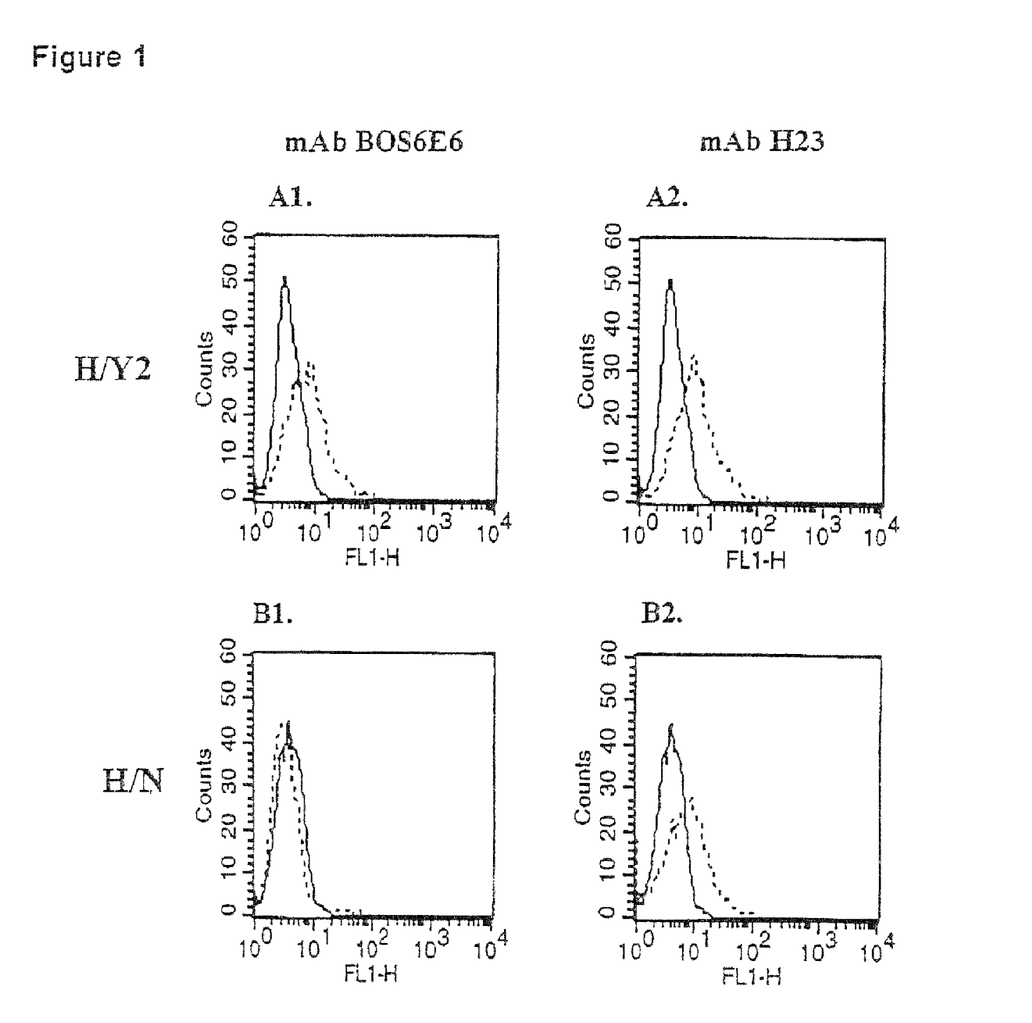
FIG. 1 demonstrates expression of MUC1 proteins in epithelial cell transfectants. HBL-100 cells were transfected either with (A) the expression vector harboring the MUC1/Y cDNA (H/Y2) or (B) with the selection plasmid pSV2neo (H/N). The expression of the various MUC1 isoforms was analyzed by incubating the different transfectants using the (A1, B1), anti-MUC1/Y specific mAb BOS6E6/2 or (A2, B2) anti-tandem-repeat mAb H23.

To generate MUC1/Y expressing cells, an epithelial cell line, HBL-100, was co-transfected with an eukaryotic expression vector harboring the MUC1/Y cDNA and the selection plasmid pSV2neo. Control cells were generated by transfecting cells only with the neomycin-resistance conferring plasmid. Following transfections, many control transfectants (H/N) were generated and a solitary clone (H/Y2), which consistently expressed MUC1/Y protein. The expression was confirmed by flow cytometry analyses, using the anti-MUC1/Y mAbs (FIG. 1).

As can be seen from the above flow cytometry analyses, both the H/Y2 and the H/N transfectants express endogenous MUC1 tandem-repeat-array-containing isoforms.

Example 2

Figure 2:
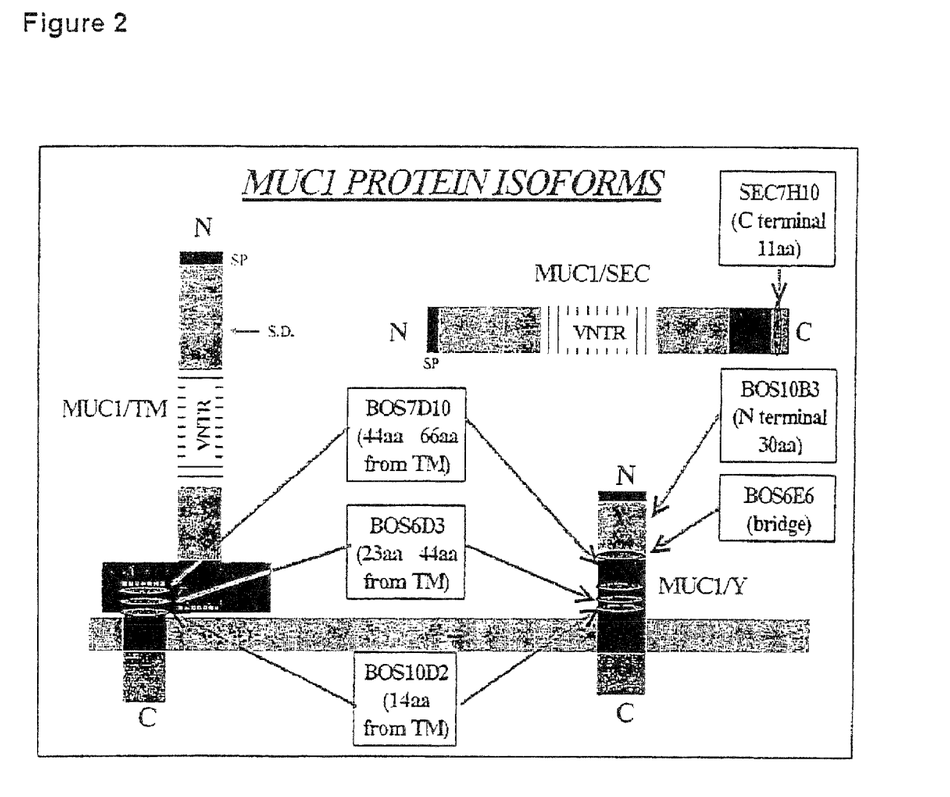
FIG. 2 shows the different MUC1 protein isoforms and the location of the epitopes of the monoclonal specific antibodies.

Effects of Monoclonal Antibodies Recognizing the MUC1/Y and MUC1/SEC Proteins on Epithelial Cell Viability A number of antibodies directed against the MUC1 protein have been used. The regions of their immunoreactivity within the MUC1 proteins have been defined (FIG. 2).

To assess the effect that anti-MUC1/Y and anti MUC1/SEC monoclonal antibodies exert on human epithelial cell growth, MUC1/Y expressing human epithelial cell transfectants (H/Y2) were seeded in wells that had been previously coated with serum-free hybridoma supernatants which contained either anti-MUC1/Y (four mAbs which recognize different epitopes in the MUC1/Y extracellular domain) or an anti-MUC1/SEC monoclonal antibody.

Figure 3B:
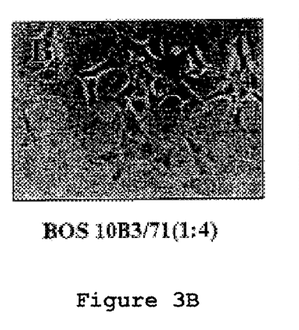
Figure 3C:
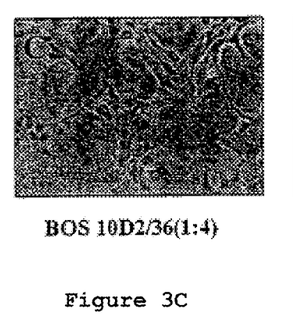

A dramatic effect was observed when the cells were plated on wells coated with the monoclonal antibody BOS7D10 (FIG. 3A columns 2 and 2' and panel C). The other three anti-MUC1/Y monoclonal antibodies were without any discernible effect (FIG. 3A columns 1 and 1', 3 and 3', 4 and 4', and panels B and C). The potent inhibitory effect of hybridoma BOS7D10 on cell growth was still observed following an eight-fold dilution of the serum-free hybridoma supernatant and was only titrated out at a final sixteen-fold dilution.

Similar results were observed when the antibodies were tested with MCF7 human breast cancer cells as the target cells. Also in this case, the monoclonal antibody BOS7D10 exerted a potent cell death activity on the MCF7 cells. The other antibodies were without any noticeable effect on the cells.

Figure 3D:
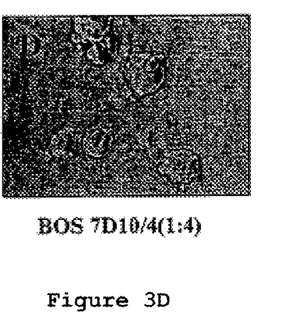

As was demonstrated in FIG. 3D, microscope analysis revealed that the cells that were treated with BOS7D10 had a different appearance than cells that were treated with other antibodies (FIG. 3B,C). In fact they exhibit a morphology of non-viable cells.

Figure 4:
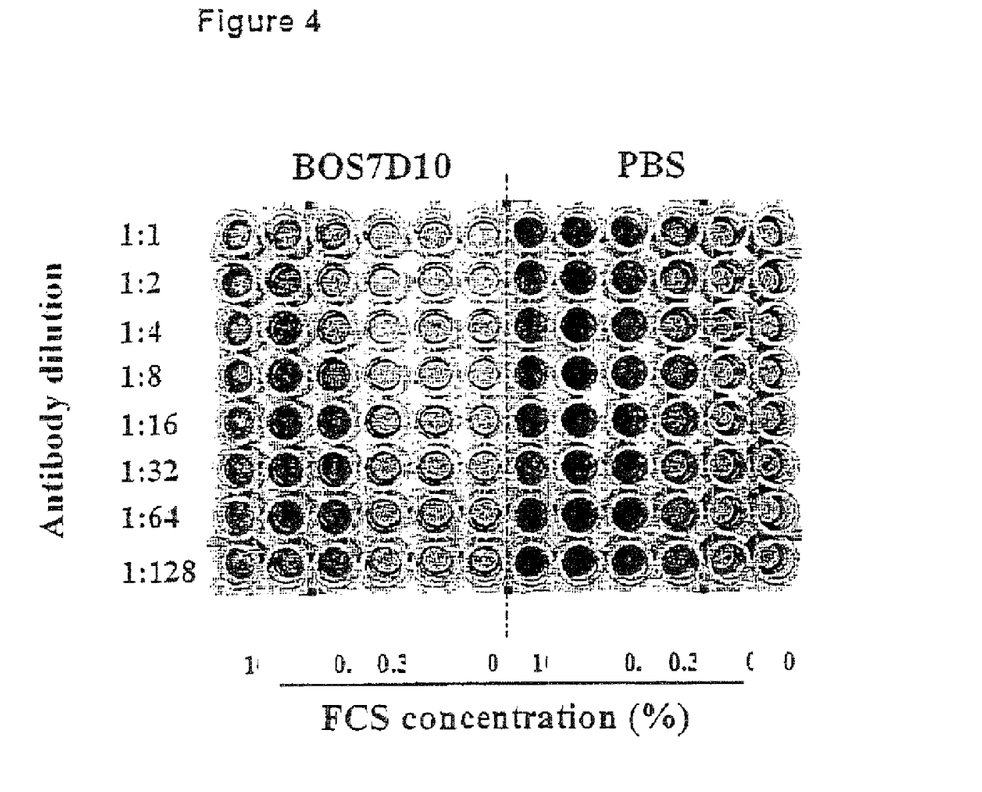
FIG. 4 shows that the effect of BOS7D10 on cell growth is dependent on serum concentration. H/Y2 cells were exposed to medium supplemented with 0.1% (lanes 6; 12); 0.2% (lanes 5; 11); 0.3% (lanes 4; 10); 1% (lanes 3; 9); 3% (lanes 2; 8); and 10% (lanes 1; 7) FCS. The effect of the different mAb on the H/Y2 cells was analyzed by MTT in order to measure the inhibitory effect of mAbs on cell proliferation.

A "box" titration of the BOS7D10 hybridoma supernatant (FIG. 4) versus the concentration of fetal calf serum demonstrated that the cell-growth inhibitory activity could be clearly observed when cells were grown at a final serum concentration of 0.3% and was also discernible, albeit to a lesser extent, at a 1% final serum concentration (FIG. 4). Growth of cells at serum concentrations higher than 1% abrogated the growth inhibitory activity exerted by the BOS7D10 antibodies.

Interestingly, the monoclonal antibody SEC7H10, directed against the eleven C-terminal amino acids of the MUC1/SEC protein, also demonstrated growth-inhibitory-activity (FIG. 3A columns 5 and 5'). This growth inhibition was, however, considerably less than that exerted by BOS7D10. A control monoclonal antibody isotype matched for the BOS7D10 and SEC7H10 antibodies was without any effect (data not shown).

Example 3

Effects of Anti-MUC1/Y and Anti-MUC1/SEC Antibodies on the Binding of MUC1/Y and MUC1/SEC In parallel to the effect of the anti-MUC1/Y and anti-MUC1/SEC antibodies on epithelial cell growth, we analyzed whether these antibodies could affect, in any way, the binding of MUC1/SEC for the MUC/Y protein (see Methods for description of the assay).

The antibody BOS7D10, which recognizes an epitope in the extracellular domain of MUC1/Y markedly enhanced the binding of MUC1/Y to the MUC1/SEC protein. The anti-MUC1/SEC antibody SEC7H10 also increased the binding, albeit to a lesser extent than BOS7D10 (see table 1). The other antibodies did not effect the MUC1/Y MUC1/SEC interaction in the same way (table 1). Intriguingly, these results are in direct correlation to the antibodies effect on cell growth. BOS7D10, which elicits the highest cell-growth inhibition, has also a potent effect on MUC1/Y MUC1/SEC interaction. Similar correlation was shown for SEC7H10. It appears that antibodies that increase MUC1/Y-MUC1/SEC binding may elicit a negative growth signal. This conclusion tallies well with previous data suggesting that MUC1/SEC binding to MUC1/Y may exert a growth-inhibitory signal. Indeed addition of conditioned medium containing the MUC1/SEC protein to cells expressing the MUC1/Y protein reduced the growth rate of the latter cells as well as inducing morphological alteration of cells (53) that was accompanied by actin filament degradation that correlates with apoptotic processes. Furthermore, coinoculation of highly tumorigenic mouse mammary tumor cells engineered to express the MUC1/Y protein with MUC1/SEC expressing cells markedly reduced the tumor growth of the injected cells (a reduction of 67%) suggesting that the presence of MUC1/SEC within the microenvironment of the injected highly tumorigenic mouse mammary tumor cells diminishes their tumor-forming ability

TABLE 1

Effect of anti-MUC1 mAbs on the MUC1/SEC-MUC1/Y interaction and on cell death

| | BOS 7D10/4 | BOS 10D2/36 | BOS 6E6/2 | BOS 10B3/71 | SEC 7H10/5 |
|---|---|---|---|---|---|
| Effect on the MUC1/SEC-MUC1/Y interaction | ↑↑ | ↓ | N.E. | ↓ | ↑ |
| Cell death effect | + + | − | − | − | + |

The effect of anti-MUC1 mAbs on the MUC1/SEC-MUC1/Y interaction was analyzed by a sandwich ELISA assay (described in Methods).

REFERENCES

1. Keydar I, Chou C S, Hareuveni M, Tsarfaty I, Sahar E, Selzer G, Chaitchik S and Hizi A., Production and characterization of monoclonal antibodies identifying breast tumor-associated antigens. *Proc Natl Acad Sci USA*, 86, 1362-6.(1989).
2. Schumacher U and Adam E, Immunohistochemical detection of the MUC1 gene product in human cancers grown in scid mice. *J Histochem, Cytochem.*, 46, 127-34 (1998).
3. Bork, P. and Patthy, L. The SEA module: a new extracellular domain associated with O-glucosilation *Protein Sci.* 4:1421-4 (1995).
4. Baruch A, Hartman M, Zrihan-Licht S, Greenstein S, Burstein M, Keydar I, Weiss M, Smorodinsky N and Wreschner D H. Preferential expression of novel MUC1 tumor antigen isoforms in human epithelial tumors and their tumor-protecting function. *Int. J. Cancer* 71, 741-9 (1998).
5. Baruch A, Hartman M, Yoeli M, Adereth Y, Greenstein S, Stadler Y, Skornik Y, Zaretsky J, Smorodinsky N I, Keydar I and Wreschner D H. The breast cancer-associated MUC1 gene generates both a receptor and its cognate binding protein. *Cancer Res.* 59, 1552-61 (1999).
6. Zrihan-Licht S, Baruch A, Elory-Stein O, Keydar I and Wreschner D H. Tyrosine phosphorylation of the MUC1 breast cancer membrane proteins. Cytokine receptor-like molecules. *FEBS Lett* 356, 130-6 (1994).
7. Stancovski I, Hurwith E, Leitner O, Ulrich A, Yarden Y and Sela M. Mechnistic aspects of the opposing effects of monoclonal antibodies to the ERBB receptor on tumor growth. *Proc. Natal. Acad. Sci. USA* 88, 8691-5 (1991).
8. Ward E S, Gussow D, Griffiths A D, Jones P T and Winter G. Binding activities of a repertoire of single immunoglobulin variable domains secreted from *Escherichia coli*. *Nature* 341, 544-6 (1989).
9. Bird R E, Hardman K D, Jacobson S, Kaufman B M, Lee T, Pope S H, Riordan G S and Whitlow M. Single-chain antigen-binding protein. *Science* 242, 423-6 (1988).
10. Huston J S, Levinson D, Mudgett-Hunter M, Tai M S, Novotny J, Margolies M N, Ridge R J, Bruccoleri R E, Haber E, Crea R, et al Protein engineering of antibody binding sites: recovery of specific activity in an anti-digoxin single-chain Fv analogue produced in *Escherichia coli*. *PNAS USA* 85, 5879-83 (1988).
11. Hollinger P, Prospero T and Winter G. "Diabodies": small bivalent and bispecific antibody fragments. *PNAS USA* 90, 6444-8 (1982).
12. Forresen et al, *Cancer Res.* 52, 3255-61 (1992).
13. Perez-Soler r and Priebe W. Anthracycline antibodies with high liposome entrapment: structural features and biological activity. *Cancer Res.* 50, 4260-6 (1990).
14. Khokhar A R, al-Baker S, Brown T and Perez-Soler R. Chemical and biological studies on a series of lipid-soluble (trans-(R,R)- and -(S,S)-1,2-diaminocyclohexane) platinum (II) complexes incorporated in liposomes. *J. Med. Chem.* 34, 325-9 (1991).
15. Bordin A and Nyqvist-Mayer A. In vitro release studies on lidocaine aqueous, micellar solutions, and o/w emulsions. *Acta. Pharm. Suec.* 19, 267-284 (1982).
16. Lasic D D. Mixed micelles in drug delivery. *Nature* 335, 279-280 (1992).
17. Supersaxo A, Hein W R and Steffen H. mixed micelles as a proliposomal, lymphotropic drug carrier. *Pharm. Res.* 8, 1286-91 (1991).
18. Fung B M, O'Rear E A, Afzal J, Frech C B, Mamrosh D L and Gangoda M Perfluorochemical emulsions with fluorinated surfactants and anticancer drugs. *Biomater. Artif. Cells Artif. Organs* 16, 439 (1988).
19. Yokoyama M, Okano T, Sakurai Y, Ekimoto H, Shibazaki C and Kataoka K. Toxicity and antitumor activity against solid tumors of micelle-forming polymeric anticancer drug and its extremely long circulation in blood. *Cancer Res.* 51, 3229-36 (1991).
20. Gaffney E V A cell line (HBL-100) established from human breast milk. *Cell Tissue Res.* 227, 563-8 (1982).
21. southern PJ and Berg P Transformation of mammalian cells to antibiotic resistance with a bacterial gene under control of the SV40 early region promoter. *J. Mol. Appl. Gent.* 1, 32741 (1982).

SEQ ID NO 1:
(N-terminus) SVV VQLTLAFREG TINVHDVETQ FNQYKTEAAS

RYNLTISDVS VSDVPFPFSA QSGAGV (C-terminus)

What is claimed is:

1. A method of selectively inhibiting mammalian cell proliferation or cell growth, comprising causing a cell which expresses MUC1 protein isoform to come into contact with an effective amount of an antibody which specifically binds to an epitope within a transmembrane isoform of MUC1 protein to selectively inhibit mammalian cell proliferation or cell growth, wherein said epitope is an amino acid sequence within the 59 residue amino acid sequence of SEQ ID No. 1.

2. The method according to claim 1, wherein said cell is a cancer cell.

3. The method of claim 2, wherein said cancer cell is an epithelial cancer cell.

4. The method of claim 3, wherein said epithelial cancer cell is a breast cancer cell, an ovarian cancer cell, a lung cancer cell or a colon cancer cell.

5. The method of claim 1, wherein said MUC1 isoform is MUC1/Y, MUC1/REP, or MUC1/X.

6. The method of claim 1, wherein said antibody is a monoclonal antibody, a synthetic antibody, a polyclonal antibody or a chimera.

7. The method of claim 1, wherein said antibody is conjugated to a cytotoxic drug.

8. The method of claim 1, wherein the selective inhibition of mammalian cell proliferation or cell growth selectively induces mammalian cell death.

9. The method of claim 1, wherein the step of causing the cell to come into contact with the antibody comprises administering an effective amount of the antibody to a subject in need thereof.

10. The method of claim 9, wherein the effective amount of the antibody is administered to treat a disease involving the pathological proliferation of cells.

11. A method of treating a subject with a disease involving pathological proliferation of cells, comprising the step of administering to a subject in need an effective amount of a peptide which comprises an amino acid sequence corresponding to the extracellular region of a transmembrane isoform of MUC1 protein, so as to induce an increase in the level of antibodies specific for said peptide in the subject, thereby treating the disease, wherein said peptide comprises an amino acid sequence within the 59 residue amino acid sequence of SEQ ID No. 1.

12. The method of claim 11, wherein said MUC1 isoform is MUC1/Y, MUC1/REP, or MUC1/X.

* * * * *

SEQUENCE LISTING

```
<160> NUMBER OF SEQ ID NOS: 3

<210> SEQ ID NO 1
<211> LENGTH: 59
<212> TYPE: PRT
<213> ORGANISM: Homo sapiens
<220> FEATURE:
```

```
<221> NAME/KEY: MISC_FEATURE
<223> OTHER INFORMATION: Figure 6

<400> SEQUENCE: 1

Ser Val Val Gln Leu Thr Leu Ala Phe Arg Glu Gly Thr Ile Asn
1               5                   10                  15

Val His Asp Val Glu Thr Gln Phe Asn Gln Tyr Lys Thr Glu Ala Ala
                20                  25                  30

Ser Arg Tyr Asn Leu Thr Ile Ser Asp Val Ser Val Ser Asp Val Pro
            35                  40                  45

Phe Pro Phe Ser Ala Gln Ser Gly Ala Gly Val
    50                  55

Figure 5:
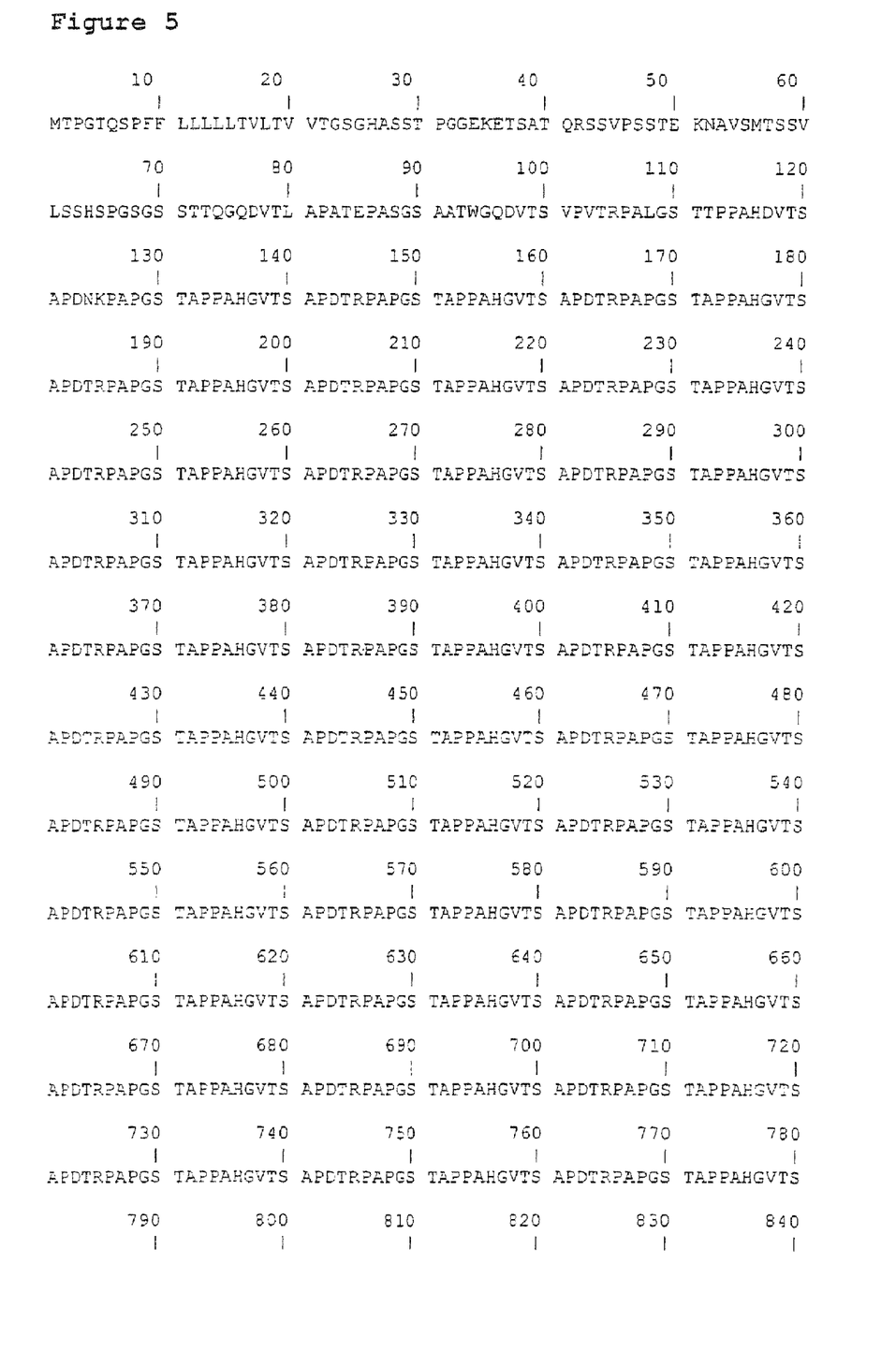
FIG. 5 shows the sequence of MUC1/REP protein SEQ ID NO:2).

<210> SEQ ID NO 2
<211> LENGTH: 1255
<212> TYPE: PRT
<213> ORGANISM: Homo sapiens
<220> FEATURE:
<221> NAME/KEY: MISC_FEATURE
<223> OTHER INFORMATION: Figure 5 - MUC1/REP protein

<400> SEQUENCE: 2

Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
                20                  25                  30

Gly Glu Lys Glu Thr Ser Ala Thr Gln Arg Ser Ser Val Pro Ser Ser
            35                  40                  45

Thr Glu Lys Asn Ala Val Ser Met Thr Ser Ser Val Leu Ser Ser His
    50                  55                  60

Ser Pro Gly Ser Gly Ser Ser Thr Thr Gln Gly Gln Asp Val Thr Leu
65                  70                  75                  80

Ala Pro Ala Thr Glu Pro Ala Ser Gly Ser Ala Ala Thr Trp Gly Gln
                85                  90                  95

Asp Val Thr Ser Val Pro Val Thr Arg Pro Ala Leu Gly Ser Thr Thr
            100                 105                 110

Pro Pro Ala His Asp Val Thr Ser Ala Pro Asp Asn Lys Pro Ala Pro
        115                 120                 125

Gly Ser Thr Ala Pro Pro Ala His Gly Val Thr Ser Ala Pro Asp Thr
    130                 135                 140

Arg Pro Ala Pro Gly Ser Thr Ala Pro Pro Ala His Gly Val Thr Ser
145                 150                 155                 160

Ala Pro Asp Thr Arg Pro Ala Pro Gly Ser Thr Ala Pro Pro Ala His
                165                 170                 175

Gly Val Thr Ser Ala Pro Asp Thr Arg Pro Ala Pro Gly Ser Thr Ala
            180                 185                 190

Pro Pro Ala His Gly Val Thr Ser Ala Pro Asp Thr Arg Pro Ala Pro
        195                 200                 205

Gly Ser Thr Ala Pro Pro Ala His Gly Val Thr Ser Ala Pro Asp Thr
    210                 215                 220

Arg Pro Ala Pro Gly Ser Thr Ala Pro Pro Ala His Gly Val Thr Ser
225                 230                 235                 240

Ala Pro Asp Thr Arg Pro Ala Pro Gly Ser Thr Ala Pro Pro Ala His
                245                 250                 255

Gly Val Thr Ser Ala Pro Asp Thr Arg Pro Ala Pro Gly Ser Thr Ala
            260                 265                 270
```

```
Pro Pro Ala His Gly Val Thr Ser Ala Pro Asp Thr Arg Pro Ala Pro
            275                 280                 285

Gly Ser Thr Ala Pro Pro Ala His Gly Val Thr Ser Ala Pro Asp Thr
        290                 295                 300

Arg Pro Ala Pro Gly Ser Thr Ala Pro Pro Ala His Gly Val Thr Ser
305                 310                 315                 320

Ala Pro Asp Thr Arg Pro Ala Pro Gly Ser Thr Ala Pro Pro Ala His
                325                 330                 335

Gly Val Thr Ser Ala Pro Asp Thr Arg Pro Ala Pro Gly Ser Thr Ala
            340                 345                 350

Pro Pro Ala His Gly Val Thr Ser Ala Pro Asp Thr Arg Pro Ala Pro
            355                 360                 365

Gly Ser Thr Ala Pro Pro Ala His Gly Val Thr Ser Ala Pro Asp Thr
        370                 375                 380

Arg Pro Ala Pro Gly Ser Thr Ala Pro Pro Ala His Gly Val Thr Ser
385                 390                 395                 400

Ala Pro Asp Thr Arg Pro Ala Pro Gly Ser Thr Ala Pro Pro Ala His
                405                 410                 415

Gly Val Thr Ser Ala Pro Asp Thr Arg Pro Ala Pro Gly Ser Thr Ala
            420                 425                 430

Pro Pro Ala His Gly Val Thr Ser Ala Pro Asp Thr Arg Pro Ala Pro
            435                 440                 445

Gly Ser Thr Ala Pro Pro Ala His Gly Val Thr Ser Ala Pro Asp Thr
        450                 455                 460

Arg Pro Ala Pro Gly Ser Thr Ala Pro Pro Ala His Gly Val Thr Ser
465                 470                 475                 480

Ala Pro Asp Thr Arg Pro Ala Pro Gly Ser Thr Ala Pro Pro Ala His
                485                 490                 495

Gly Val Thr Ser Ala Pro Asp Thr Arg Pro Ala Pro Gly Ser Thr Ala
            500                 505                 510

Pro Pro Ala His Gly Val Thr Ser Ala Pro Asp Thr Arg Pro Ala Pro
            515                 520                 525

Gly Ser Thr Ala Pro Pro Ala His Gly Val Thr Ser Ala Pro Asp Thr
        530                 535                 540

Arg Pro Ala Pro Gly Ser Thr Ala Pro Pro Ala His Gly Val Thr Ser
545                 550                 555                 560

Ala Pro Asp Thr Arg Pro Ala Pro Gly Ser Thr Ala Pro Pro Ala His
                565                 570                 575

Gly Val Thr Ser Ala Pro Asp Thr Arg Pro Ala Pro Gly Ser Thr Ala
            580                 585                 590

Pro Pro Ala His Gly Val Thr Ser Ala Pro Asp Thr Arg Pro Ala Pro
            595                 600                 605

Gly Ser Thr Ala Pro Pro Ala His Gly Val Thr Ser Ala Pro Asp Thr
        610                 615                 620

Arg Pro Ala Pro Gly Ser Thr Ala Pro Pro Ala His Gly Val Thr Ser
625                 630                 635                 640

Ala Pro Asp Thr Arg Pro Ala Pro Gly Ser Thr Ala Pro Pro Ala His
                645                 650                 655

Gly Val Thr Ser Ala Pro Asp Thr Arg Pro Ala Pro Gly Ser Thr Ala
            660                 665                 670

Pro Pro Ala His Gly Val Thr Ser Ala Pro Asp Thr Arg Pro Ala Pro
            675                 680                 685

Gly Ser Thr Ala Pro Pro Ala His Gly Val Thr Ser Ala Pro Asp Thr
```

-continued

```
            690                 695                 700
Arg Pro Ala Pro Gly Ser Thr Ala Pro Ala His Gly Val Thr Ser
705                 710                 715                 720

Ala Pro Asp Thr Arg Pro Ala Pro Gly Ser Thr Ala Pro Pro Ala His
            725                 730                 735

Gly Val Thr Ser Ala Pro Asp Thr Arg Pro Ala Pro Gly Ser Thr Ala
                740                 745                 750

Pro Pro Ala His Gly Val Thr Ser Ala Pro Asp Thr Arg Pro Ala Pro
            755                 760                 765

Gly Ser Thr Ala Pro Pro Ala His Gly Val Thr Ser Ala Pro Asp Thr
770                 775                 780

Arg Pro Ala Pro Gly Ser Thr Ala Pro Pro Ala His Gly Val Thr Ser
785                 790                 795                 800

Ala Pro Asp Thr Arg Pro Ala Pro Gly Ser Thr Ala Pro Pro Ala His
            805                 810                 815

Gly Val Thr Ser Ala Pro Asp Thr Arg Pro Ala Pro Gly Ser Thr Ala
                820                 825                 830

Pro Pro Ala His Gly Val Thr Ser Ala Pro Asp Thr Arg Pro Ala Pro
            835                 840                 845

Gly Ser Thr Ala Pro Pro Ala His Gly Val Thr Ser Ala Pro Asp Thr
850                 855                 860

Arg Pro Ala Pro Gly Ser Thr Ala Pro Pro Ala His Gly Val Thr Ser
865                 870                 875                 880

Ala Pro Asp Thr Arg Pro Ala Pro Gly Ser Thr Ala Pro Pro Ala His
            885                 890                 895

Gly Val Thr Ser Ala Pro Asp Thr Arg Pro Ala Pro Gly Ser Thr Ala
                900                 905                 910

Pro Pro Ala His Gly Val Thr Ser Ala Pro Asp Thr Arg Pro Ala Pro
            915                 920                 925

Gly Ser Thr Ala Pro Pro Ala His Gly Val Thr Ser Ala Pro Asp Asn
930                 935                 940

Arg Pro Ala Leu Gly Ser Thr Ala Pro Pro Val His Asn Val Thr Ser
945                 950                 955                 960

Ala Ser Gly Ser Ala Ser Gly Ser Ala Ser Thr Leu Val His Asn Gly
            965                 970                 975

Thr Ser Ala Arg Ala Thr Thr Thr Pro Ala Ser Lys Ser Thr Pro Phe
            980                 985                 990

Ser Ile Pro Ser His His Ser Asp Thr Pro Thr Thr Leu Ala Ser His
            995                 1000                1005

Ser Thr Lys Thr Asp Ala Ser Ser Thr His His Ser Ser Val Pro
    1010                1015                1020

Pro Leu Thr Ser Ser Asn His Ser Thr Ser Pro Gln Leu Ser Thr
    1025                1030                1035

Gly Val Ser Phe Phe Phe Leu Ser Phe His Ile Ser Asn Leu Gln
    1040                1045                1050

Phe Asn Ser Ser Leu Glu Asp Pro Ser Thr Asp Tyr Tyr Gln Glu
    1055                1060                1065

Leu Gln Arg Asp Ile Ser Glu Met Phe Leu Gln Ile Tyr Lys Gln
    1070                1075                1080

Gly Gly Phe Leu Gly Leu Ser Asn Ile Lys Phe Arg Pro Gly Ser
    1085                1090                1095

Val Val Val Gln Leu Thr Leu Ala Phe Arg Glu Gly Thr Ile Asn
    1100                1105                1110
```

-continued

```
Val His Asp Val Glu Thr Gln Phe Asn Gln Tyr Lys Thr Glu Ala
    1115            1120             1125

Ala Ser Arg Tyr Asn Leu Thr Ile Ser Asp Val Ser Val Ser Asp
    1130            1135             1140

Val Pro Phe Pro Phe Ser Ala Gln Ser Gly Ala Gly Val Pro Gly
    1145            1150             1155

Trp Gly Ile Ala Leu Leu Val Leu Val Cys Val Leu Val Ala Leu
    1160            1165             1170

Ala Ile Val Tyr Leu Ile Ala Leu Ala Val Cys Gln Cys Arg Arg
    1175            1180             1185

Lys Asn Tyr Gly Gln Leu Asp Ile Phe Pro Ala Arg Asp Thr Tyr
    1190            1195             1200

His Pro Met Ser Glu Tyr Pro Thr Tyr His Thr His Gly Arg Tyr
    1205            1210             1215

Val Pro Pro Ser Ser Thr Asp Arg Ser Pro Tyr Glu Lys Val Ser
    1220            1225             1230

Ala Gly Asn Gly Gly Ser Ser Leu Ser Tyr Thr Asn Pro Ala Val
    1235            1240             1245

Ala Ala Ala Ser Ala Asn Leu
    1250            1255

<210> SEQ ID NO 3
<211> LENGTH: 10
<212> TYPE: PRT
<213> ORGANISM: Homo sapiens

<400> SEQUENCE: 3

Ile Lys Phe Arg Pro Gly Ser Val Val Val
1               5                   10
```